United States Patent
Nau et al.

(10) Patent No.: US 6,268,396 B1
(45) Date of Patent: Jul. 31, 2001

(54) USE OF VALPROIC ACID ANALOG FOR THE TREATMENT AND PREVENTION OF MIGRAINE AND AFFECTIVE ILLNESS

(75) Inventors: Heinz Nau, Hannover (DE); Emer Leahy, Tarrytown; Alan O'Connell, Babylon, both of NY (US)

(73) Assignee: American Biogenetic Sciences, Inc., Copiague, NY (US)

( * ) Notice: Subject to any disclaimer, the term of this patent is extended or adjusted under 35 U.S.C. 154(b) by 0 days.

(21) Appl. No.: 09/337,986

(22) Filed: Jun. 22, 1999

Related U.S. Application Data
(60) Provisional application No. 60/090,281, filed on Jun. 22, 1998.

(51) Int. Cl.$^7$ ................................................ A61K 31/185
(52) U.S. Cl. ............................................................ 514/578
(58) Field of Search ............................................ 514/578

(56) References Cited

U.S. PATENT DOCUMENTS

| | | |
|---|---|---|
| 3,325,361 | 6/1967 | Meunier . |
| 3,701,729 | 10/1972 | Fischer et al. . |
| 3,847,956 | 11/1974 | Silbert et al. . |
| 3,932,285 | 1/1976 | Ceprini et al. . |
| 4,025,649 | 5/1977 | Taillandier et al. . |
| 4,129,599 | 12/1978 | Escher et al. . |
| 5,021,398 | 6/1991 | Sharma et al. . |
| 5,503,830 | 4/1996 | Nekrasov et al. . |
| 5,681,854 | 10/1997 | Pang et al. . |
| 5,786,380 * | 7/1998 | Nau et al. .............................. 514/557 |

FOREIGN PATENT DOCUMENTS

| | | |
|---|---|---|
| 0 632 008 B1 | 4/1998 | (EP) . |
| 2599737 | 12/1987 | (FR) . |
| 56-80116 | 7/1981 | (JP) . |
| 59-67266 | 4/1984 | (JP) . |
| 1-135740 | 5/1989 | (JP) . |
| 6-188152 | 7/1994 | (JP) . |
| WO 94 06743 | 3/1994 | (WO) . |
| WO 94/06456 | 3/1994 | (WO) . |
| WO 94/12608 | 6/1994 | (WO) . |
| WO 95/33044 | 12/1995 | (WO) . |
| WO 98/03472 | 1/1998 | (WO) . |

OTHER PUBLICATIONS

Ca127 :156131, Tran et al, J. Pharm Technol. 13(4), 163–168, abstract, 1997.*

Communication From Australian Patent Office Concerning Section 27(1) Filing By Ono Pharmaceutical Company Limited Aug. 26, 1998.

Atkinson, R.S., et al., Intramolecular Reactions of N–Nitrenes: Description of the Transition State Geometry for Addition to Alkenes, *J. Chem. Soc., Perkin Trans.* 1:1135–45 (1987).

Atkinson, R.S., et al., Intramolecular Reactions of N–Nitrenes with Alkenes, *J. Chem. Soc., Perkin Trans.* 1:1905–12 (1984).

Barton, H, et al., Photochemical Degradation of Barbituric Acid Derivatives, *Pharmazie,* 38:630–1 (1983).

Baxter, G.P.,. Thirty–Sixth Annual Report of the Committee on Atomic Weights. Determinations Published During 1929, *J. Am. Chem. Soc.,* 52:1281–1283 (1930).

Borstlap, C., 2–Alkylalkanoic Acids: Relation Between Structure and Sensitivity Towards Water Hardness, *Chem. Phys. Chem. Anwendungstech. Grenzflaechenaktiven Stoffe, Ber. Int. Knogr.,* 6$^{th}$, 1:91–9 (1973).

Breusch, F.L., et al., Isomeric Series of the DI–N–Alkylacetic Acids $C_{23}H_{46}O_2$, *Second Chemical Institute of the University of Istanbul, Series C.,* 33:39–42 (1968).

Chapman, A.G., et al., Acute Anticonvulsant Activity of Structural Analogues of Valporic Acid and Changes in Brain Gaba and Aspartate Content, *Life Sciences,* 32:2023–2031 (1983).

Curran, D.P., et al., Amide–Based Protecting/Radical Translocating (PRT) Groups. Generation of Radicals Adjacent to Carbonyls by 1,5–Hydrogen Transfer Reactions of O–Iodoanilides, *Tetrahedron,* 50:7343–66 (1994).

Doyle et al. (1993) J. Neurochem. 61:266–272.

Doyle and Regan (1993) J. Neural Transm. 92:33–39.

Drake, C.A., et al., Synthesis of Ethylenes with Acyclic Quaternary Carbons by Dehydration of Neopentyl Alcohols. Application of the 2–D Inapt Techniques, *J. Org. Chem.,* 53:4555–62 (1988).

Fu, G.C., et al., Catalytic Ring–Closing Methathesis of Functionalized Dienes by a Ruthenium Carbene Complex, *J. Am. Chem. Soc.* 115:9856–7 (1993).

Gavrilova, V. M., et al., Side Reactions in Hydrocarboxylation of Olefins, *Translated from Zhurnal Prikladnoi Khimii,* 63:1428–1431 (1990).

Haj–Yehia, Abdulla and Bialer, Meir (1990) J. Pharm. Sci. 79:8, 719–724.

Hauck and Nau (1989) Toxicol. Lett. 49:41–48.

Hauck and Nau (1989) Toxicol. Lett. 60:145–153.

Kato, K., et al., Thromboxane Synthetase Inhibitors (TXSI). Design, Synthesis, and Evaluation of a Novel Series of $\omega$–Pyridylalkenoic Acids, *J. Med. Chem.,* 28:287–94 (1985).

(List continued on next page.)

Primary Examiner—Rebecca Cook
(74) Attorney, Agent, or Firm—Morgan & Finnegan, L.L.P.

(57) ABSTRACT

This invention relates to a method for the treatment and prevention of migraine and affective illness by administering a therapeutically effective amount of the valproic acid analog 2-n-propyl-4-hexynoic acid. The compound 2-n-propyl-4-hexynoic acid is an effective anti-migraine and anti-affective illness drug with greatly reduced adverse effects including neurotoxicity and teratogenic potential compared to valproic acid. This invention thus provides an improved method for treating and preventing migraine and affective illness.

10 Claims, No Drawings

OTHER PUBLICATIONS

Keane, P.E., et al., The Effects of Analogues of Valproic Acid on Seizures Induced by Pentylenetetrazol and Gaba Content in Brain of Mice, *Neuropharmacology.* 22:875–879 (1983).

Konen, D.A., et al., $_\alpha$ Anions. VII. Direct Oxidation of Enolate Anions to 2–Hydroperoxy—and 2–Hydroxycarboxylic Acids and Esters, *J. Org. Chem.,* 40:3253–8 (1975).

Kotva, R., et al., Some 2–Substituted Derivatives of 5–(2–Amino–6–Hydroxy–4–Oxo–3, 4–Dihydro–5–Pyrimidinyl)–Pentanoic Acid, *Collection Czechoslovak Chem. Commun.* 46:1397–404 (1981).

Kurata, K., et al., Synthesis of Alkl–3 $_\delta$–Lactones V. Synthesis of Alkyl–3 $_{\delta-Lactones,}$ *Chem. Pharm. Bull.,* 24:538–40 (1976).

Kurth, M.J., et al., Regioselectivity in the Iodolactonization of 1,6–Heptadien–4–Carboxylic Acid Derivatives, *Tetrahedron Lett.,* 29:1517–20 (1988).

Kurth, Mark J. and Brown, Edward G., (1987) J. Am. Chem. Soc., 109(22), 6844–5.

Lambert, C., et al., "Palladium (II) Catalyzed Cyclization of Alkynoic Acids", *Tetrahedron Lett.,* 25:5323–6 (1984).

Lindau, J., et al., Thermal Phase Behaviour of Thallium (L) Branched Alkanoates—Influence of Chain Length and Position of Branching Löscher, W. and Nau, H., (1985) Neuropharmacology 24:5, 427–435.

Maguire, C. and Regan, C.M., (1991) Int. J. Devl. Neuroscience 9:6 581–586.

Martin, M.L. and Regan, C.M., (1991) Brain Research, 554:223–228.

Martin, M.L. and Regan, C.M., (1998) Brain Research, 459:131–137.

Martin, M.L. and Regan, C.M., (1998) Toxic In Vitro, 2:1 43–38.

McCarty, F.J., et al., Synthesis and Pharmacology of a Series of 1–Aralkyl–3–Butenylamines, *J. Med. Chem.,* 11:534–41 (1968).

Mellow, A.M., et al., Sodium Valproate in the Treatment of Behavioral Disturbance in Dementia, *J. Geriatric Psychiatry and Neurology,* 6:205–209 (1993).

Mysak, A.E., et al. Gas–Chromatographic Analysis of Branched Carboxylic Acids Formed on Carboxylating $C_6$—$C_{10}$ $_\alpha$—Olefins, *Journal of Analytical Chemistry of the USSR,* 25:1729–1731 (1970).

Nau, H. and Löscher, W., (1986) Fund. Applied Toxicol. 6:669–676.

Nau et al.., (1981) J. Pharmacol. Exp. Ther. 219:768–777.

Nau, H. and Löscher, W., (1986) Fund. Applied Toxicol. 69:310–321.

Negret, G.R., et al.; Asymmetric Alkylations of N–Acyl Dihydropyrimidinones; *Tetrahedron Asymetry* 2:105–108 (1991).

Okada, Katshuhide, et al., (1980) Agric. Biol. Chem., 44(11), 2595–2599.

Padwa, A., et al., Ligand Effects on Dirhodium (II) Carbene Reactivities. Highly Effective Switching Between Competitive Carbenoid Transformations, *J. Am. Chem. Soc.,* 115:8669–80 (1993).

Regan, C.M., Brain Research, 347:394–398 1987.

Regan, et al. (1991) Toxic. In Vitro 5:77–82.

Rougon, et al., (1986) J. Cell Biol. 103:2429–2437.

Sangster, J., Octanol–Water Partition Coefficients of Simple Organic Compounds, *J. Phys. Chem.* 18: 1111–1229 (1989).

Saus, A., et al., On the Preparation of the Stereoisomeric Hydroxymethylpentadecanes, *Tenside,* 6:129–30 (1969).

Shostenko, A.G., et al., Radiation–Induced Interaction of Ethylene with Carboxylic Acids, *Translated from Khimiya Vyzokikh Energii* [*High–Energy Chemistry*] 10:371–373 (1976).

Sonnet, Philip E., Syntheses of the Stereoisomers of the Sex Pheromones of the Southern Corn Rootworm and Lesser Tea Tortrix, *J. Org. Chem.,* 47:3793–6 (1982).

Spencer, R.W., et al., Ynenol Lactones: Synthesis and Investigation of Reactions Relevant to their Inactivation of Serine Proteases, *J. Am. Chem. Soc.,* 108:5589–97 (1986).

Ställberg, G.; Syntheses of Substituted Glycerol Ehters; *Chemica Scripta,* 7:31–41 (1975).

Stanients, V.I., et al., Conformational Effects in Iodolactonization of Anions of $_\alpha$–R–Allylacetic Acids, Translation of *Dokl. Akad. Nauk SSSR,* 187:109–111 (1969) @ pp. 525–527 of the English Edition of that Journal.

Wilson, Stephen R., (1993) Proc. Workshop Vitam. D., $6^{th}$ (Vitam. D.), 749–754, New York University, NY, NY 10003.

Yoshishu, K., et al., The Proceedings for the $23^{rd}$ Symposium on Essences, Terpenes and Essential–Oil Chemistry, *Koryo, Terupen oyobi Seiyu Kagaku ni kansuru Toronkai,* $23^{rd,}$ 157–8 (1979).

Zambelli, A., et al., Carbon–13 Nuclear Magnetic Resonance Analysis of Model Compounds of Saturated End Groups in Polypropylene, *Macromolecules,* 12:154–6 (1979).

\* cited by examiner

USE OF VALPROIC ACID ANALOG FOR THE TREATMENT AND PREVENTION OF MIGRAINE AND AFFECTIVE ILLNESS

This application claims priority to U.S. provisional application Ser. No. 60/090,281, filed Jun. 22, 1998.

FIELD OF THE INVENTION

This invention relates to the valproic acid analog 2-n-propyl-4-hexynoic acid, and to its use for the treatment and prevention of migraine and affective illness. The valproic acid analog of the present invention is believed to be an effective anti-migraine and anti-affective illness drug with greatly reduced adverse effects including neurotoxicity and teratogenic potential compared to valproic acid. This invention thus provides an improved method for treating and preventing migraine and affective illness.

BACKGROUND OF THE INVENTION

Migraine is defined as a periodically occurring vascular headache characterized by pain in the head (usually unilateral), nausea and vomiting, photophobia, phonophobia, vertigo and general weakness. Migraine is the most common type of vascular headache and affects as many as 15% of the world's population. Of the different types of migraines, classical migraine and common migraine are the two most prevalent. The major difference between the two types of migraines is that classical migraines are preceded by the appearance of neurological symptoms before an attack whereas common migraines are not preceded by such symptoms. Migraine is caused by intermittent brain dysfunction. However, the precise pathophysiological mechanisms involved are not understood. The head pain is believed to involve blood vessel dilation and a reduction in the brain's pain-relieving chemicals.

Analgesics are often used to treat infrequent and mild migraines. Analgesics reduce the pain of a migraine and in the case of aspirin also discourage clumping of blood platelets. However, for moderate to severe migraines, stronger medications such as ergotamine and valproic acid are necessary. Ergotamine tartrate is a vasoconstrictor which counteracts the painful dilation stage of the headache. When taken during the early stages of an attack, ergotamine tartrate helps to relieve the classic and common migraine symptoms. Valproic acid has been shown to be effective in both the treatment and prevention of migraine, however, its mechanism of anti-migraine action is unclear. It is believed that valproic acid increases brain gamma-aminobutyric acid (GABA) levels and in doing so may activate the GABA receptor and suppresses migraine-related events.

A relationship has been reported between migraine, affective illness and epilepsy. Although the three disorders are distinct, they all are paroxysmal dysregulations of the nervous system that partially overlap in their pharmacology. Some drugs, such as valproic acid, are effective in treating all three syndromes, suggesting the presence of shared underlying pathophysiology, while other drugs are effective for treating one syndrome. For example, beta blockers which are effective against migraine are not useful for treating the other two syndromes and may even exasperate depression.

The kindling model for complex-partial seizures is based on the progressive development of seizures combined with electroencephalographic (EEG) paroxysmal patterns induced by repeated initially subconvulsive electrical stimulation of limbic structures, e.g. the basolateral nucleus of the amygdala. Once established, the phenomenon persists for months. Since the amygdala kindled seizures in animals share numerous characteristics with complex-partial seizures in humans, it is presently the best animal model of complex partial seizures (Goddard et al. 1969; Löscher and Schmidt 1988; Löscher 1993). One major advantage of using the amygdala kindling model is that both behavioral and EEG parameters of the partial and generalized seizures can be measured. Furthermore, the amygdala kindling model is reported to be appropriate for studying diseases such as migraine, affective illness and epilepsy which increase in severity overtime and in a manner which is related to the number of symptomatic episodes.

Previously, the valproic acid analog 2-n-propyl-4-hexynoic acid was shown to be an improved antiepileptic compared to valproic acid by the subcutaneous pentetrazole convulsion test (PTZ test). Experimental findings from various studies in which both the PTZ test and the amygdala kindling test were employed indicate that drugs that are effective against the PTZ induced seizures are not necessarily effective against amygadala kindled seizures and vice versa (Loscher, W., and Honack, Dagmar., *Eur. J. Pharmacol.* (1993), 232:147–158; Johnson, D. et al., *Epilepsy Res.* (1991), 8:64–70). Therefore, not all anticonvulsant are effective against amygdala kindled seizures. In other words, drugs that are antiepileptics are not necessarily effective in the treatment of migraine or affective illness.

Recent publications suggest that the amygdala kindling model is appropriate for studying shared mechanisms underlying the increase in severity over time of symptomatic episodes in epilepsy, migraine and affective illness (R. Post and S. Silberstein, *Neurology* (1994), 44: S37–S47; R. Post and S. Weiss, *Molecular Neurobiology* (1996), 13:33–60). In amygdala kindling, intermittent electrical stimulation of the amygdala of the brain is first without effect, but eventually following repeated stimulation, results in increasing biochemical and physiological responses cumulating in a full-blown convulsion. Following continued triggering of seizures, seizures begin to emerge spontaneously. This progression of symptom severity involves a long-lasting change in the property of the neuron. Experimental findings indicate that kindling induced in animals shares many features with human affective illness, migraine and epilepsy, such as progression from triggered to spontaneous, changes in behavior patterns during the seizure and responsiveness to certain anti-seizure drugs. Therefore, amygdala kindling may serve as a model to study the possible underlying mechanisms for the memory-like processes that may be involved in migraine, affective illness and epilepsy.

U.S. Pat. No. 4,942,182 reports the stage dependent sensitivity to drug treatment of seizures induced by amygdala kindling. In this model, carbamazepine suppresses complete amygdala-kindled seizures in rats, but is ineffective in preventing their development. Diazepam however, which is effective in inhibiting the earlier stages of seizure development is not effective during the late stages when seizures occur spontaneously. Phenytoin, another anticonvulsant drug has activity opposite that of diazepam being an effective block of spontaneous seizures, but not seizures elicited during the early stages of kindling.

The amygdala kindling model is also an important model to evaluate potentially useful drugs because it can provide information different from that of other seizure models. For example, whereas carbamazepine is an effective anticonvulsant in several seizure models including the amygdala kindling model, it is less effective on seizures induced by pentylenetetrazole and high dose picrotoxin.

Valproic acid is an effective drug for the treatment and prevention of epilepsy, migraine and affective illness.

However, it has a short duration of action, and suffers from serious side effects such as sedation, potentially fatal hepatotoxicity and tertogenicity. There has been a considerable effort to discover analogs of valproic acid that are equally effective, but have a longer duration of activity and a greater margin of safety. One study has demonstrated that the valproic acid analog 2-n-propyl-4-hexynoic acid is an effective antiepileptic with a longer duration of activity and greatly reduced sedative and teratogenic effects compared to valproic acid (Nau et al, U.S. application Ser. No. 08/344, 810, which is hereby incorporated in its entirety by reference). The compound 2-n-propyl-4-hexynoic acid is therefore an improved antiepileptic. However, since the compound was only examined in the subcutaneous pentetrazole convulsion test (PTZ test) which is designed to evaluate the effectiveness of drugs against epilepsy, the effectiveness of the compound for the treatment of migraine or affective illness is not known.

SUMMARY OF THE INVENTION

This invention relates to the compound 2-n-propyl-4-hexynoic acid, pharmaceutical compositions containing this compound, and their use to treat and/or prevent migraine and affective illness. The compound for use in this invention is believed to be effective in the treatment and prevention of migraine and affective illness, and exhibits greatly reduced adverse effects and longer duration of activity, when compared to valproic acid.

One object of this invention is to provide a method for treating and/or preventing migraine and affective illness (including unipolar, bipolar illness and acute mania) due to a variety of causes, by administering to an individual in need of such treatment a therapeutically or prophylactically effective amount of 2-n-propyl-4-hexynoic acid.

Another object of this invention is to provide pharmaceutical compositions for the treatment and/or prevention of migraine and affective illness that has longer duration of activity, exhibits lower adverse effects, and avoids teratogenic toxicity compared to valproic acid.

DETAILED DESCRIPTION OF THE INVENTION

This invention relates to the use of the valproic acid analog 2-n-propyl-4-hexynoic acid as a treatment and prevention for migraine and affective illness.

This invention provides a method of treating and preventing migraine or affective illness in individuals by administering 2-n-propyl-4-hexynoic acid. The synthesis and desirable metabolic properties of 2-n-propyl4-hexynoic acid are fully disclosed in U.S. Pat. No. 5,786,380 (Examples 7–8 and 10–11) which is incorporated herein by reference in its entirety. Mammals, and in particular humans, who would benefit from this method of treatment include those exhibiting, or at risk for exhibiting, any type of recurring headaches, especially vascular headaches and those which are moderate or severe. Individuals suffering from migraine are expected to benefit from administration of 2-n-propyl-4-hexynoic acid. The method of the invention comprises administering to an individual a therapeutically effective amount of 2-propyl-4-hexynoic acid which is sufficient to reduce or prevent migraine or affective illness.

In contrast to valproic acid, the compound for use with this invention exhibits greatly reduced adverse effects and teratogenicity, and has a longer duration of activity.

The data presented here show that like valproic acid, 2-n-propyl-4-hexynoic acid is expected to be effective against amygdala kindled seizures. Furthermore, it exhibits adverse effects only at the highest dose tested and those effects are much milder compared to that of valproic acid. Therefore, 2-propyl-4-hexynoic acid provides an improved method for the treatment and prevention of migraine and affective illness.

The compound 2-propyl-4-hexynoic acid is effective for the treatment of acute mania with bipolar disorder. Typical manic symptoms include pressure of speech, motor hyperactivity, reduced need for sleep, flight of ideas, grandiosity, poor judgement, aggressiveness, and possible hostility.

The compound 2-propyl-4-hexynoic acid is also effective for the prevention and treatment of migraine headaches.

It will be apparent to those skilled in the art that the compound 2-propyl-4-hexynoic acid for use with this invention may exist in enantiomeric forms. Pure enantiomers may be resolved from the racemate by methods well known in the art. Alternatively, enantiomeric forms may be prepared by chiral synthesis. Individual R and S enantiomers, racemates and non-racemic mixtures of enantiomers of 2-n-propyl-4-hexynoic acid are all within the scope of this invention. When the individual enantiomers are used, the S enantiomer of 2-n-propyl-4-hexynoic acid is preferred if one needs to take advantage of the apparent higher pharmacokinetic profile of the S enantiomer. However, if maximal avoidance of teratogenic side effects is required, then the R enantiomer is the preferred form.

The dose of the compound used in the treatment of such disease will vary in the usual way with the seriousness of the disorder, the weight and metabolic health of the sufferer. The preferred initial dose for the general patient population will be determined by routine dose-ranging studies, as are conducted for example during clinical trials. Therapeutically effective doses for individual patients may be determined by titrating the amount of drug given to the individual to arrive at the desired therapeutic or prophylactic effect while minimizing side effects. Dosages may be similar to those used with valproic acid, however, they may be adjusted appropriately, based on the potencies and kinetic parameters disclosed herein or as determined by routine methods. A preferred initial dose for this compound, may be estimated to be between about 1 and 60 mg/kg/day, more preferably between 10–20 mg/kg/day. The preferred plasma concentration for patients taking 2-n-propyl-4-hexynoic acid is between 50–100 ug/ml.

Administration of the compounds of this invention may be by any method used for administering therapeutics, such as for example oral, parenteral, intravenous, intramuscular, subcutaneous, or rectal administration.

This invention also provides pharmaceutical compositions for the treatment of migraine. In addition to comprising the compound 2-n-propyl-hexynoic acid or a salt or pro-drug thereof, the pharmaceutical composition may also comprise additives such as preservatives, excipients, fillers, wetting agents, binders, disintegrants, buffers, and/or carriers. Suitable additives may be for example magnesium and calcium carbonates, carboxymethylcellulose, starches, sugars, gums, magnesium or calcium stearate, coloring or flavoring agents, and the like. There exists a wide variety of pharmaceutically acceptable additives for pharmaceutical dosage forms, and selection of appropriate additives is a routine matter for those skilled in art of pharmaceutical formulation.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose. Unit dose forms for oral administration may be tablets, capsules, and the like, and may contain conventional excipients such as binding agents, for example syrup, acacia, gelatin, sorbitol, tragacanth, or polyvinylpyrrolidone; and carriers or fillers, for example lactose, sugar, maize-starch, calcium phosphate, sorbitol or glycine. Additives may include disintegrants, for example starch, polyvinylpyrrolidone, sodium starch glycolate or microcrystalline cellulose; preservatives, and pharmaceutically acceptable wetting agents such as sodium lauryl sulphate.

In addition to unit dose forms, multi-dosage forms are also contemplated to be within the scope of the invention. Delayed-release compositions, for example those prepared by employing slow-release coatings, micro-encapsulation, and/or slowly-dissolving polymer carriers, will also be apparent to those skilled in the art, and are contemplated to be within the scope of the invention.

The solid oral compositions may be prepared by conventional methods of blending, filling, tabletting or the like. Repeated blending operations may be used to distribute the active agent throughout those compositions employing large quantities of fillers. Such operations are conventional in the art. The tablets may be coated according to methods well known in normal pharmaceutical practice, for example with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol syrup, methyl cellulose, gelatin, hydroxyethylcellulose, carboxymethylcellulose, aluminum stearate gel, and hydrogenated edible fats; emulsifying agents, for example lecithin, sorbitan monooleate, or acacia; non-aqueous vehicles (which may include edible oils), for example almond oil or fractionated coconut oil, oily esters such as esters of glycerine, propylene glycol, or ethyl alcohol; preservatives, for example methyl or propyl p-hydroxybenzoate or sorbic acid; and if desired conventional flavoring or coloring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water or saline for injection and filter sterilized before filling into a suitable vial or ampoule and sealing. Advantageously, additives such as a local anaesthetic, preservative and buffering agent can be dissolved in the vehicle. Suitable buffering agents are, for example, phosphate and citrate salts. To enhance the stability, the composition can be frozen after filling into the vial and the water removed under vacuum. Parenteral suspensions are prepared in substantially the same manner, except that the compound is suspended in the vehicle instead or being dissolved, and sterilization cannot be accomplished by filtration. The compound can be sterilized by conventional means, for example by exposure to radiation or ethylene oxide, before being suspended in the sterile vehicle. Advantageously, a surfactant or wetting agent is included in the composition to facilitate uniform distribution of the compound.

The present invention will now be described by way of examples, which are meant to illustrate, but not limit, the scope of the invention.

EXAMPLE 1

In Example 1, the anti-migraine and anti-affective illness profiles of 2-n-propyl-4-hexynoic acid and valproic acid are compared in the amygdala kindling model.

Materials and Methods

Animals

Female Wistar rats (Harlan-Winkelmarm, Borchen, Germany) were obtained at an age of 11–12 weeks (body weight 180–200 g). Female rats were employed because they are known to eliminate drugs less rapidly than do males, which was thought to be an advantage for drug potency studies. Rats were kept separately in plastic cages at controlled temperature (23° C.) and humidity (about 50%) with a 12-h light cycle beginning at 7 a.m. They received standard diet (Altromin; Lage, F.R.G.), tap water and libitum. All drug injections were done in the afternoon at an ambient temperature of 23–25° C. The regular protocol started by taking the rats out of their individual cage, weighing them and joining them together on a table with six open plastic cages for better behavioral observations. Therefore animals were able to move from one cage to another and either to have social contact or to avoid it. After a short adaptation time of approximately 15 minutes, rectal body temperatures were recorded followed by drug or vehicle application.

Amygdala-kindling in rats

For implantation of stimulation and recording electrodes, rats were anesthetized with chloral hydrate (360 mg/kg i.p.) and received stereotaxic implantation (according to the surgery methods described in the atlas of Paxinos and Watson [1986]) of one bipolar electrode in the right basolateral amygdala. Coordinates for electrode implantation were AP-2.2 mm, L-4.8 mm, V-8.5 mm. All coordinates were measured from bregma. Skull screws served as the indifferent reference electrode. The electrode assembly was attached to the skull by dental acrylic cement. After a postoperative period of 2 weeks, constant current stimulations (500 $\mu A$, 1 ms, monophasic square-wave pulses, 50/s for 1 s) were delivered to the amygdala at intervals of 1/day until ten stage 5 seizures were elicited. The electrical susceptibility of the stimulated region (threshold for induction of afterdischarges) was recorded on the first day of the experiment (initial afterdischarge threshold) as well as after kindling acquisition (with an interval of at least 4 days after the tenth stage 5 seizure) using an ascending staircase procedure. The initial current intensity was 10 $\mu A$, and the current intensity was increased in steps of about 20% of the previous current at intervals of 1 min until an afterdischarge of at least 3 s duration was elicited. Since almost all fully kindled animals exhibited generalized seizures (stage 4–5) at the afterdischarge threshold current, it was not necessary to determine the threshold for generalized seizures separately. In addition to afterdischarge threshold, the following parameters of kindled seizures were measured in fully-kindled rats after stimulation with the afterdischarge threshold current: seizure severity was classified according to Racine (1972): 1-immobility, eye closure, twitching of vibrissae, sniffing, facial clonus; 2-head nodding associated with more severe facial clonus; 3-clonus of one forelimb; 4-rearing, often accompanied by bilateral forelimb clonus; 5-rearing with loss of balance and falling accompanied by generalized clonic seizures. Seizure duration 1 (SD 1) was the duration of limbic (stage 1–2) and/or motor seizures (stage 3–5). Seizure duration 2 (SD 2) included the time of limbic and/or motor seizures plus the adjacent time of immobility. Afterdischarge duration 1 (ADD 1) was the time of spikes in the EEG recorded from the site of stimulation with a frequency of at least 1/s. Afterdischarge duration 2 (ADD 2) was the total time of spikes occurring in the EEG including those, which followed the ADD 1 with lower frequency and amplitude.

The anti-seizure effects of 2-propyl-4-hexynoic acid and valproate in fully kindled rats were determined in a group of 8–9 rats (no. 784, 785, 787, 788, 789, 790 [had to be taken out of the trial, because of loss of electrodes], 791, 792, 793) with reproducible stage 5 seizures.

Drugs were injected 15 min prior to stimulation intraperitoneally. Control experiments were always performed 2–3 days before each drug experiment. For control determinations, rats received i.p. injections of vehicle (saline) with the pretreatment time of the respective drug experiment. For all drug experiments, at least 4 days were interposed between 2 drug injections in order to avoid alterations in drug potency due to cumulation or tolerance.

The significance of differences between pre-drug control recordings and recordings after drug injection was calculated by the Wilcoxon signed rank test for paired replicates (SigmaStat for Windows, version 1.0).

Tests used for quantification of adverse effects

In addition to recordings of anticonvulsant parameters, kindled rats were observed for adverse effects in order to estimate a therapeutic index. Tests included open field observations, rotarod test and body temperature. Tests were always performed in the same manner in control and drug experiments at two different times, just before application of drug or vehicle and 13 minutes after application.

The rotarod test was carried out with a rod of 6 cm diameter and rotation speed of 8 r.p.m. Neurological deficit was indicated by inability of the animals to maintain their equilibrium for at least 1 min on the rotating rod. Rats had to be trained prior to drug experiments to maintain their balance on the rod. After drug or vehicle treatment, rats which were not able to maintain their equilibrium on the rod for 1 minute were put again on the rod twice. Only animals which were not able to remain on the rod for three subsequent 1 minute attempts were considered to exhibit neurological deficit.

In addition to these quantitative estimations of neurological deficit, behavioral alterations observed after administration of 2-propyl-4-hexynoic acid and valproate noted in the cage and by placing the animals in an open field of 90–100 cm diameter. Muscle tone was estimated by palpation of the abdomen. The extent of deficits in behavior after administration of the compounds was determined by a rating system (Löscher et al. 1987). In short, animals were taken out of the cage, placed in an open field, observed for about 1 minute and rated separately for ataxia, abducted hindlimbs, reduced righting, flat body posture, circling, Straub tail, piloerection, hypolocomotion and hyperlocomotion (abdominal muscle tone was evaluated by palpation at the end of the period of observation). All other parameters except ataxia were scored from 0 to 3: 0—absent; 1—equivocal; 2—present; 3—intense. For ataxia (06): 1—slight ataxia in hind-legs (tottering of the hind quarters); 2—more pronounced ataxia with dragging of hind legs; 3—further increase of ataxia and more pronounced dragging of hind legs; 4—marked ataxia, animals lose balance during forward locomotion; 5—very marked ataxia with frequent loss of balance during forward locomotion; 6—permanent loss of righting reflexes, but animal still attempts to move forward. Rectal body temperature was measured by an electronic thermometer. Body weight of the animals was recorded once daily before drug injection. Significance of differences in behavior between pre-drug and post-drug data determined in the same group of animals was calculated by the Wilcoxon signed rank test for paired replicates and for body temperature by Student's paired t-test (SigmaStat for Windows, version 1.0). Differences in body temperature were always compared only within the experimental day with the pre-drug time as control to one post-drug time.

Test drugs

The compound 2-propyl-4-hexynoic acid (MW 154) was melted in a water bath at 40° C. for approximately 30 min and then transferred to an equimolar volume of 1 molar NaOH of similar temperature. After formation of the sodium salt it was dissolved in saline to a volume of 2.5 ml/kg in rats, and 10 ml/kg in mice, respectively. Valproate (dissolved in water as sodium salt) was a gift of Desitin Arzneimittel GmbH, Hamburg, Germany. The stock solution had a concentration of 100 mg/ml (calculated as free acid) and was therefore dissolved in saline to receive equivalent injection volumes as for 2-propyl-4-hexynoic acid. All drug doses given in this study refer to the free (acid) forms.

Since there were differences in potencies between both compounds, plasma was obtained from rats immediately after treatment and kindling stimulation during one dose experiment.

RESULTS

Amygdala-kindling and adverse effects in rats

Both compounds were tested at the following doses in fully amygdala-kindled rats: 50, 75, 100, and 200 mg/kg i.p. after 15 min pretreatment time. For valproate significant effects against amygdala-kindled seizures (Tables 1–4) were observed at all doses tested. The lower doses of 50 and 75 mg/kg i.p. increased the threshold significantly by means of 109% and 77%, respectively. At 100 mg/kg i.p. significant effects on all kindling parameters were observed. The average electrical threshold for induction of after discharges was increased by 319% (Table 3). If all rats would have been stimulated at 20% above their individual threshold only (which several groups use as kindling stimulus), all rats would have been totally protected against seizures. Seizure severity was significantly decreased from 5.0 to 3.0. Seizure duration was reduced from an average of 81 to 18 s and total afterdischarge duration (ADD 2) was reduced from 95 to 20 s. No alterations in behavior and body-temperature were observed. Rotarod test was performed without failure.

With 200 mg/kg valproate the response to the kindling parameters increased with threshold increase of 970%, decrease of seizure severity from 4.9 to 1.6, reduction of seizure duration from 73 to 9 s and reduction of afterdischarge duration from 106 to 9 s (Table 4). As expected from earlier experiments this dosage was combined with several adverse effects like obvious ataxia (average score 2.8 after 13 min pretreatment time), hypolocomotion (1.0), muscle relaxation (2.0) and wet dog shakes. The rotarod-test on the other hand was performed without failure. Body-temperature increased up to 39.2° C.

TABLE 1

Anti-Seizure Activity And Adverse Effects of Valproate At 50 mg/kg

| animal | | 784 | 785 | 787 | 788 | 789 | 790 | 791 | 792 | 793 | X | S.E.M. | stat. sign |
|---|---|---|---|---|---|---|---|---|---|---|---|---|---|
| KINDLING | | | | | | | | | | | | | Wilcoxon |
| afterdisch.thresh | control | 30 | 20 | 30 | 15 | 36 | 20 | 42 | 42 | 25 | 28.89 | 3.26 | |
| (ADT; µA) | compound | 50 | 110 | 36 | 75 | 42 | 75 | 60 | 60 | 36 | 60.44 | 7.93 | 0.002 |
| seizure severity | control | 5 | 5 | 5 | 5 | 5 | 5 | 5 | 5 | 5 | 5.00 | 0.00 | |
| (SS; score) | compound | 4 | 5 | 1 | 4 | 5 | 5 | 5 | 5 | 5 | 4.33 | 0.44 | n.s |
| seizure duration1 | control | 60 | 71 | 30 | 80 | 65 | 71 | 52 | 84 | 88 | 66.78 | 5.98 | |
| (SD1; sec) | compound | 58 | 64 | 6 | 95 | 88 | 73 | 83 | 95 | 88 | 72.22 | 9.36 | n.s |
| seizure duration2 | control | 279 | 244 | 122 | 283 | 250 | 242 | 123 | 245 | 256 | 227.11 | 20.37 | |
| (SD2; sec) | compound | 320 | 214 | 6 | 314 | 268 | 280 | 198 | 245 | 240 | 231.67 | 31.37 | n.s |
| afterdisch.dur.1 | control | 161 | 68 | 30 | 80 | 65 | 71 | 52 | 94 | 88 | 78.78 | 12.10 | |
| (ADD1; sec) | compound | 67 | 83 | 6 | 107 | 88 | 73 | 83 | 95 | 88 | 76.67 | 9.64 | n.s |
| afterdisch.dur.2 | control | 161 | 78 | 30 | 80 | 65 | 71 | 52 | 94 | 88 | 79.89 | 12.03 | |
| (ADD2; sec) | compound | 67 | 83 | 6 | 107 | 88 | 73 | 83 | 95 | 88 | 76.67 | 9.64 | n.s |
| BODY TEMP. | (° C.) | | | | | | | | | | | | t-test |
| control day | ante appl. | 38.8 | 39.0 | 38.5 | 39.1 | 38.8 | 38.7 | 38.9 | 39.0 | 38.9 | 38.86 | 0.06 | control |
| | 13' post appl. | 38.7 | 38.6 | 38.7 | 38.80 | 38.7 | 38.8 | 39.0 | 38.7 | 38.7 | 38.71 | 0.05 | n.s. |
| day of exper. | ante appl. | 38.8 | 39.1 | 38.5 | 39.1 | 39.1 | 38.6 | 38.4 | 38.7 | 38.8 | 38.79 | 0.09 | control |
| | 13' post appl. | 38.7 | 39.0 | 38.7 | 39.0 | 38.8 | 38.7 | 39.0 | 39.0 | 38.5 | 38.82 | 0.06 | n.s |
| BEHAVIOR | (score) | | | | | | | | | | | | |
| antaxia (1–6) | 13' | ' | | | | | | | | | | | |
| abduct. hindlimb (1–3) | 13' | | | | | | | | | | | | |
| red. righting (1–3) | 13' | | | | | | | | | | | | |
| (flat body posture) (1–3) | 13' | | | | | | | | | | | | |
| circling (1–3) | 13' | | | | | | | | | | | | |
| Straub tail (1–3) | 13' | | | | | | | | | | | | |
| pilorection (1–3) | 13' | | | | | | | | | | | | |
| hypolocomotion (1–3) | 13' | | | | | | | | | | | | |
| hyperlocomotion (1–3) | 13' | | | | | | | | | | | | |
| muscle relaxation (1–3) | 13' | | | | | | | | | | | | |
| rotarod-test day of exper. | 13' | + | + | + | + | + | + | + | + | + | 0% | | |

TABLE 2

Anti-Seizure Activity And Adverse Effects of Valproate At 75 mg/kg

| animal | | 784 | 785 | 787 | 788 | 789 | 791 | 792 | 793 | X | S.E.M. | Signifikanz |
|---|---|---|---|---|---|---|---|---|---|---|---|---|
| KINDLING | | | | | | | | | | | | Wilcoxon |
| afterdisch.thresh. | control | 20 | 30 | 25 | 15 | 50 | 50 | 110 | 30 | 41.25 | 10.80 | |
| (ADT; µA) | compound | 50 | 75 | 60 | 25 | 110 | 60 | 130 | 75 | 73.13 | 11.80 | 0.0039 |
| seizure severity | control | 5 | 5 | 5 | 5 | 5 | 5 | 5 | 5 | 5.00 | 0.00 | |
| (SS; score) | compound | 4 | 5 | 4 | 5 | 2 | 3 | 5 | 5 | 4.13 | 0.40 | n.s. |
| seizure duration1 | control | 47 | 68 | 84 | 65 | 81 | 41 | 70 | 92 | 68.50 | 6.24 | |
| (SD1; sec) | compound | 20 | 65 | 65 | 95 | 9 | 18 | 60 | 100 | 54.00 | 12.36 | n.s |
| seizure duration2 | control | 267 | 218 | 202 | 327 | 348 | 120 | 266 | 100 | 249.75 | 25.46 | |
| (SD2; sec) | compound | 30 | 445 | 300 | 343 | 9 | 18 | 392 | 465 | 250.75 | 70.19 | n.s |
| afterdisch.dur.1 | control | 94 | 77 | 125 | 64 | 86 | 41 | 82 | 92 | 82.63 | 8.59 | |
| (ADD1; sec) | compound | 20 | 87 | 95 | 104 | 9 | 18 | 102 | 103 | 67.25 | 15.26 | n.s. |
| afterdisch.dur.2 | control | 94 | 77 | 125 | 64 | 86 | 41 | 82 | 92 | 82.63 | 8.59 | |
| (ADD2;sec) | compound | 20 | 87 | 95 | 104 | 9 | 18 | 102 | 103 | 67.25 | 15.26 | n.s. |
| BODY TEMP. | (° C.) | | | | | | | | | | | t-Test |
| control day | ante appl. | 38.5 | 38.2 | 38.8 | 37.8 | 37.8 | 38.9 | 38.2 | 38.5 | 38.34 | 0.15 | control |
| | 13' post appl. | 38.7 | 38.8 | 38.9 | 38.9 | 38.9 | 39.1 | 38.4 | 39.0 | 38.84 | 0.08 | 0.0103 |
| day of exper. | ante appl. | 38.6 | 38.2 | 38.1 | 38.1 | 38.8 | 38.8 | 38.4 | 38.8 | 38.48 | 0.11 | control |
| | 13' post appl. | 38.7 | 39.0 | 38.6 | 38.4 | 37.4 | 39.2 | 38.4 | 38.7 | 38.55 | 0.19 | n.s. |

TABLE 2-continued

Anti-Seizure Activity And Adverse Effects of Valproate At 75 mg/kg

| animal | | 784 | 785 | 787 | 788 | 789 | 791 | 792 | 793 | X | S.E.M. | Signifikanz |
|---|---|---|---|---|---|---|---|---|---|---|---|---|
| BEHAVIOR | (score) | | | | | | | | | | | |
| antaxia (1–6) | 13' | | | | | | | | | | | |
| abduct. hindlimb (1–3) | 13' | | | | | | | | | | | |
| red. righting (1–3) | 13' | | | | | | | | | | | |
| (flat body posture) (1–3) | 13' | | | | | | | | | | | |
| circling (1–3) | 13' | | | | | | | | | | | |
| Straub tail (1–3) | 13' | | | | | | | | | | | |
| pilorection (1–3) | 13' | | | | | | | | | | | |
| hypolocomotion (1–3) | 13' | | | | | | | | | | | |
| hyperlocomotion (1–3) | 13' | | | | | | | | | | | |
| muscle relaxation (1–3) | 13' | | | | | | | | | | | |
| rotarod-test day of exper. | 13' | + | + | + | + | + | + | + | + | 0% | | |

TABLE 3

Anti-Seizure Activity And Adverse Effects of Valproate At 100 mg/kg

| animal | | 784 | 785 | 787 | 788 | 789 | 790 | 791 | 792 | 793 | X | S.E.M. | stat. sign |
|---|---|---|---|---|---|---|---|---|---|---|---|---|---|
| KINDLING | | | | | | | | | | | | | Wilcoxon |
| afterdisch.thresh. | control | 30 | 10 | 20 | 15 | 36 | 10 | 90 | 90 | 25 | 36.22 | 10.57 | |
| (ADT; $\mu A$) | compound | 75 | 130 | 60 | 200 | 130 | 160 | 240 | 240 | 130 | 151.67 | 21.63 | 0.0020 |
| seizure severity | control | 5 | 5 | 5 | 5 | 5 | 5 | 5 | 5 | 5 | 5.00 | 0.00 | |
| (SS; score) | compound | 2 | 3 | 3 | 3 | 2 | 4 | 2 | 5 | 3 | 3.00 | 0.33 | 0.0039 |
| seizure duration1 | control | 60 | 55 | 70 | 65 | 92 | 91 | 138 | 77 | 85 | 81.44 | 8.33 | |
| (SD1; sec) | compound | 22 | 5 | 5 | 13 | 6 | 5 | 6 | 84 | 18 | 18.22 | 8.49 | 0.0039 |
| seizure duration2 | control | 260 | 205 | 218 | 241 | 153 | 216 | 238 | 280 | 303 | 234.89 | 14.72 | |
| (SD2; sec) | compound | 22 | 5 | 5 | 13 | 6 | 5 | 6 | 310 | 18 | 43.44 | 33.40 | 0.0039 |
| afterdisch.dur.1 | control | 60 | 5 | 70 | 65 | 92 | 91 | 138 | 77 | 85 | 81.44 | 8.33 | |
| (ADD1; sec) | compound | 22 | 5 | 5 | 13 | 6 | 5 | 6 | 100 | 18 | 20.00 | 10.22 | 0.0039 |
| afterdisch.dur.2 | control | 145 | 55 | 107 | 65 | 92 | 91 | 138 | 77 | 85 | 95.00 | 10.17 | |
| (ADD2; sec) | compound | 22 | 5 | 5 | 13 | 6 | 5 | 6 | 100 | 18 | 20.00 | 10.22 | 0.0039 |
| BODY TEMP. | (° C.) | | | | | | | | | | | | t-test |
| control day | ante appl. | 38.4 | 38.9 | 38.3 | 37.6 | 38.4 | 37.6 | 38.0 | 38.6 | 39.0 | 38.31 | 0.17 | control |
| | 13' post appl. | 38.0 | 39.0 | 38.5 | 38.7 | 38.5 | 38.6 | 37.9 | 38.3 | 38.8 | 38.48 | 0.12 | n.s. |
| day of exper. | ante appl. | 38.4 | 38.5 | 38.0 | 38.5 | 38.4 | 37.8 | 38.5 | 38.2 | 38.9 | 38.36 | 0.11 | control |
| | 13' post appl. | 38.9 | 38.9 | 38.9 | 39.0 | 39.0 | 39.1 | 39.2 | 38.9 | 38.8 | 38.97 | 0.04 | 0.0013 |
| BEHAVIOR | (score) | | | | | | | | | | | | |
| antaxia (1–6) | 13' | | | | | | | | | | | | |
| abduct. hindlimb (1–3) | 13' | | | | | | | | | | | | |
| red. righting (1–3) | 13' | | | | | | | | | | | | |
| (flat body posture) (1–3) | 13' | | | | | | | | | | | | |
| circling (1–3) | 13' | | | | | | | | | | | | |
| Straub tail (1–3) | 13' | | | | | | | | | | | | |
| pilorection (1–3) | 13' | | | | | | | | | | | | |
| hypolocomotion (1–3) | 13' | | | | | | | | | | | | |
| hyperlocomotion (1–3) | 13' | | | | | | | | | | | | |

TABLE 3-continued

Anti-Seizure Activity And Adverse Effects of Valproate At 100 mg/kg

| animal | | 784 | 785 | 787 | 788 | 789 | 790 | 791 | 792 | 793 | X | S.E.M. | stat. sign |
|---|---|---|---|---|---|---|---|---|---|---|---|---|---|
| muscle relaxation (1–3) | 13' | | | | | | | | | | | | |
| rotarod-test day of exper. | 13' | + | + | + | + | + | + | + | + | | 0% | | |

TABLE 4

Anti-Seizure Activity And Adverse Effects of Valproate At 200 mg/kg

| animal | | 784 | 785 | 787 | 788 | 789 | 791 | 792 | 793 | X | S.E.M. | stat. sign. |
|---|---|---|---|---|---|---|---|---|---|---|---|---|
| KINDLING | | | | | | | | | | | | Wilcoxon |
| afterdisch.thresh. | control | 36 | 25 | 25 | 20 | 25 | 60 | 130 | 50 | 46.38 | 12.93 | |
| (ADT; $\mu$A) | compound | 130 | 840 | 590 | 840 | 200 | 840 | 330 | 200 | 496.25 | 111.85 | 0.0039 |
| seizure severity | control | 5 | 5 | 5 | 5 | 5 | 4 | 5 | 5 | 4.88 | 0.13 | |
| (SS; score) | compound | 2 | 3 | 3 | 1 | 1 | 1 | 1 | 1 | 1.63 | 0.32 | 0.0039 |
| seizure duration1 | control | 46 | 60 | 90 | 75 | 98 | 50 | 68 | 98 | 73.13 | 7.31 | |
| (SD1; sec) | compound | 8 | 18 | 9 | 8 | 6 | 5 | 5 | 11 | 8.75 | 1.51 | 0.0039 |
| seizure duration2 | control | 321 | 229 | 338 | 241 | 361 | 232 | 298 | 295 | 289.38 | 17.87 | |
| (SD2; sec) | compound | 8 | 18 | 9 | 8 | 6 | 5 | 5 | 11 | 8.75 | 1.51 | 0.0039 |
| afterdisch.dur.1 | control | 133 | 78 | 172 | 75 | 98 | 50 | 105 | 100 | 101.38 | 13.29 | |
| (ADD1; sec) | compound | 8 | 18 | 9 | 8 | 6 | 5 | 5 | 11 | 8.75 | 1.51 | 0.0039 |
| afterdisch.dur.2 | control | 133 | 78 | 172 | 111 | 98 | 50 | 105 | 100 | 105.88 | 12.77 | |
| (ADD2; sec) | compound | 8 | 18 | 9 | 8 | 6 | 5 | 5 | 11 | 8.75 | 1.51 | 0.0039 |
| BODY TEMP. | (° C.) | | | | | | | | | | | t-Test |
| control day | ante appl. | 37.9 | 38.0 | 37.7 | 38.4 | 38.3 | 38.2 | 38.1 | 37.9 | 38.06 | 0.08 | control |
| | 13'post appl. | 37.9 | 39.0 | 38.7 | 38.2 | 38.4 | 38.7 | 38.2 | 38.5 | 38.45 | 0.12 | 0.048 |
| day of exper. | ante appl. | 38.2 | 38.5 | 39.1 | 38.6 | 38.8 | 38.9 | 38.6 | 38.9 | 38.70 | 0.10 | control |
| | 13'post appl. | 39.1 | 39.7 | 39.4 | 38.6 | 39.1 | 39.3 | 38.9 | 39.3 | 39.18 | 0.12 | 0.01 |
| BEHAVIOR | (score) | | | | | | | | | | | |
| antaxia (1–6) | 13' | 3 | 2 | 3 | 4 | 2 | 3 | 3 | 2 | 2.75 | 0.25 | 0.0039 |
| abduct. hindlimb (1–3) | 13' | | | | | | | | | | | |
| red. righting (1–3) | 13' | | | | | | | | | | | |
| (flat body posture) (1–3) | 13' | | | | | | | | | | | |
| circling (1–3) | 13' | | | | | | | | | | | |
| Straub tail (1–3) | 13' | | | | | | | | | | | |
| pilorection (1–3) | 13' | | | | | | | | | | | |
| hypolocomotion (1–3) | 13' | 1 | 1 | 1 | 1 | 1 | 1 | 1 | 1 | 1.00 | 0.00 | 0.0039 |
| hyperlocomotion (1–3) | 13' | | | | | | | | | | | |
| muscle relaxation (1–3) | 13' | 2 | 2 | 2 | 2 | 2 | 2 | 2 | 2 | 2.00 | 0.00 | 0.0039 |
| rotarod-test day of exper. | 13' | + | + | + | + | + | + | + | + | 0% | | |

In comparison, 2-propyl-4-hexynoic acid exerted no significant effects at a dose of 50 mg/kg i.p. (Table 5). At 75 mg/kg, the threshold was increased up to 109%, and the seizure severity was decreased significantly from an average score of 5.0 to 2.3 (Table 6). Seizure duration was reduced from 66 to 16 s and afterdischarge duration was reduced from 86 to 16 s. The dosage of 100 mg/kg (Table 7) increased the threshold by means of 160%. The decrease of seizure severity from 5.0 to 3.6 was less than with lower dose. The same accounts for seizure duration, which was reduced from 83 to 47 s. Maximal effects against amygdala-kindled seizures were achieved with the highest dose tested. 200 mg/kg (Table 8) increased the threshold by means of 209%, seizure severity was significantly decreased from 4.6 to 1.8. Seizure duration was reduced from an average of 62 to 19 s, and total afterdischarge duration (ADD 2) was reduced from 77 to 24 s.

Adverse effects were only observed at the highest dose of 200 mg/kg and were milder than with valproate with mild ataxia (mean score 1.5), hypolocomotion (1.4) and muscle relaxation (1.4). Body-temperatures maintained within the physiological range and rotarod-test was performed successfully by all individuals.

TABLE 5

Anti-Seizure Activity And Adverse Effects of 2-propyl-4-hexynoic acid at 50 mg/kg

| animal | | 784 | 785 | 787 | 788 | 789 | 791 | 792 | 793 | X | S.E.M. | stat. sign. |
|---|---|---|---|---|---|---|---|---|---|---|---|---|
| KINDLING | | | | | | | | | | | | Wilcoxon |
| afterdisch.thresh. | control | 42 | 20 | 25 | 15 | 36 | 20 | 60 | 42 | 25 | 31.67 | 4.82 |
| (ADT; $\mu$A) | compound | 42 | 36 | 30 | 20 | 42 | 30 | 50 | 50 | 36 | 37.33 | 3.28 | n.s. |
| seizure severity | control | 5 | 4 | 5 | 5 | 5 | 5 | 5 | 5 | 5 | 4.89 | 0.11 |
| (SS; score) | compound | 5 | 5 | 4 | 5 | 5 | 5 | 5 | 5 | 5 | 4.89 | 0.11 | n.s |
| seizure duration1 | control | 67 | 59 | 83 | 93 | 92 | 65 | 172 | 72 | 90 | 88.11 | 11.30 |
| (SD1; sec) | compound | 74 | 79 | 81 | 88 | 98 | 77 | 64 | 52 | 93 | 78.44 | 4.75 | n.s. |
| seizure duration2 | control | 289 | 121 | 282 | 335 | 253 | 174 | 260 | 293 | 280 | 254.11 | 22.01 |
| (SD2; sec) | compound | 254 | 200 | 198 | 288 | 270 | 224 | 217 | 164 | 294 | 234.33 | 14.88 | n.s |
| afterdisch.dur.1 | control | 68 | 59 | 83 | 11 | 92 | 65 | 172 | 99 | 90 | 93.22 | 11.35 |
| (ADD1; sec) | compound | 161 | 79 | 114 | 88 | 97 | 91 | 64 | 52 | 92 | 93.11 | 10.43 | n.s. |
| afterdisch.dur.2 | control | 68 | 59 | 83 | 11 | 92 | 65 | 172 | 99 | 90 | 93.22 | 11.35 |
| (ADD2; sec) | compound | 161 | 79 | 114 | 88 | 97 | 91 | 64 | 52 | 92 | 93.11 | 10.43 | n.s. |
| BODY TEMP. | (° C.) | | | | | | | | | | | | t-Test |
| control day | ante appl. | 38.0 | 38.5 | 38.1 | 37.7 | 38.6 | 38.6 | 38.4 | 38.3 | 38.8 | 38.33 | 0.12 | control |
| | 13' post appl. | 38.5 | 38.4 | 38.3 | 38.4 | 38.7 | 39.0 | 38.5 | 38.2 | 38.8 | 38.53 | 0.08 | n.s. |
| day of exper. | ante appl | 37.4 | 38.5 | 38.3 | 38.7 | 38.2 | 38.6 | 38.6 | 38.9 | 38.8 | 38.44 | 0.15 | control |
| | 13' post appl. | 37.6 | 38.9 | 38.3 | 38.3 | 38.6 | 38.5 | 38.7 | 38.6 | 38.8 | 38.48 | 0.13 | n.s. |
| BEHAVIOR | (score) | | | | | | | | | | | | |
| antaxia (1–6) | 13' | | | | | | | | | | | | |
| abduct. hindlimb (1–3) | 13' | | | | | | | | | | | | |
| red. righting (1–3) | 13' | | | | | | | | | | | | |
| (flat body posture) (1–3) | 13' | | | | | | | | | | | | |
| circling (1–3) | 13' | | | | | | | | | | | | |
| Straub tail (1–3) | 13' | | | | | | | | | | | | |
| pilorection (1–3) | 13' | | | | | | | | | | | | |
| hypolocomotion (1–3) | 13' | | | | | | | | | | | | |
| hyperlocomotion (1–3) | 13' | | | | | | | | | | | | |
| muscle relaxation (1–3) | 13' | | | | | | | | | | | | |
| rotarod-test day of exper. | 13' | + | + | + | + | + | + | + | + | | 0% | | |

TABLE 6

Anti-Seizure Activity And Adverse Effects Of 2-propyl-4-hexynoic acid at 75 mg/kg

| animal | | 784 | 785 | 787 | 788 | 789 | 791 | 792 | 793 | X | S.E.M. | stat. sign. |
|---|---|---|---|---|---|---|---|---|---|---|---|---|
| KINDLING | | | | | | | | | | | | Wilcoxon |
| afterdisch.thresh. | control | 36 | 10 | 36 | 10 | 30 | 90 | 90 | 36 | 42.25 | 11.11 | |
| (ADT; $\mu$A) | compound | 18 | 90 | 90 | 90 | 110 | 90 | 160 | 60 | 88.50 | 14.25 | 0.0157 |
| seizure severity | control | 5 | 5 | 5 | 5 | 5 | 5 | 5 | 5 | 5.00 | 0.00 | |
| (SS; score) | compound | 1 | 2 | 3 | 3 | 1 | 3 | 4 | 1 | 2.25 | 0.41 | 0.0039 |
| seizure duration1 | control | 48 | 64 | 80 | 65 | 92 | 42 | 54 | 85 | 66.25 | 6.38 | |
| (SD1; sec) | compound | 18 | 6 | 7 | 5 | 8 | 35 | 26 | 25 | 16.25 | 4.03 | 0.0039 |
| seizure duration2 | control | 348 | 240 | 210 | 180 | 120 | 230 | 398 | 260 | 248.25 | 31.48 | |
| (SD2; sec) | compound | 18 | 6 | 7 | 5 | 8 | 35 | 26 | 25 | 16.25 | 4.03 | 0.0039 |
| afterdisch.dur.1 | control | 108 | 79 | 107 | 65 | 106 | 42 | 93 | 85 | 85.63 | 8.24 | |
| (ADD1; sec) | compound | 18 | 6 | 7 | 5 | 8 | 35 | 26 | 25 | 16.25 | 4.03 | 0.0039 |
| afterdisch.dur.2 | control | 108 | 79 | 107 | 65 | 106 | 42 | 93 | 85 | 85.63 | 8.24 | |
| (ADD2; sec) | compound | 18 | 6 | 7 | 5 | 8 | 35 | 26 | 25 | 16.25 | 4.03 | 0.0039 |
| BODY TEMP. | (° C.) | | | | | | | | | | | | t-Test |
| control day | ante appl. | 38.6 | 38.9 | 39.0 | 38.7 | 38.9 | 39.2 | 39.0 | 39.2 | 38.94 | 0.08 | control |
| | 13' post appl. | 39.2 | 39.0 | 38.8 | 38.5 | 39.0 | 38.7 | 38.2 | 38.7 | 38.76 | 0.11 | n.s. |
| day of exper. | ante appl. | 37.8 | 38.2 | 38.0 | 37.9 | 38.5 | 38.3 | 37.9 | 38.4 | 38.13 | 0.09 | control |
| | 13' post appl. | 38.3 | 38.6 | 38.8 | 38.6 | 38.5 | 38.6 | 38.2 | 38.3 | 38.49 | 0.07 | 0.0133 |

TABLE 6-continued

Anti-Seizure Activity And Adverse Effects Of 2-propyl-4-hexynoic acid at 75 mg/kg

| animal | | 784 | 785 | 787 | 788 | 789 | 791 | 792 | 793 | X | S.E.M. | stat. sign. |
|---|---|---|---|---|---|---|---|---|---|---|---|---|
| BEHAVIOR | (score) | | | | | | | | | | | |
| antaxia (1–6) | 13' | | | | | | | | | | | |
| abduct. hindlimb (1–3) | 13' | | | | | | | | | | | |
| red. righting (1–3) | 13' | | | | | | | | | | | |
| (flat body posture) (1–3) | 13' | | | | | | | | | | | |
| circling (1–3) | 13' | | | | | | | | | | | |
| Straub tail (1–3) | 13' | | | | | | | | | | | |
| pilorection (1–3) | 13' | | | | | | | | | | | |
| hypolocomotion (1–3) | 13' | | | | | | | | | | | |
| hyperlocomotion (1–3) | 13' | | | | | | | | | | | |
| muscle relaxation (1–3) | 13' | | | | | | | | | | | |
| rotarod-test day of exper. | 13' | + | + | + | + | + | + | + | + | 0% | | |

TABLE 7

Anti-Seizure Activity And Adverse Effects of 2-propyl-4-hexynoic acid at 100 mg/kg

| animal | | 784 | 785 | 787 | 788 | 789 | 791 | 792 | 793 | X | S.E.M. | stat. sign. |
|---|---|---|---|---|---|---|---|---|---|---|---|---|
| KINDLING | | | | | | | | | | | | Wilcoxon |
| afterdisch.thresh. (ADT; µA) | control | 42 | 36 | 20 | 25 | 30 | 75 | 130 | 30 | 48.50 | 13.09 | |
| | compound | 60 | 130 | 75 | 200 | 110 | 200 | 160 | 75 | 126.25 | 19.79 | 0.0039 |
| seizure severity (SS; score) | control | 5 | 5 | 5 | 5 | 5 | 5 | 5 | 5 | 5.00 | 0.00 | |
| | compound | 5 | 4 | 2 | 3 | 2 | 3 | 5 | 5 | 3.63 | 0.46 | 0.0313 |
| seizure duration1 (SD1; sec) | control | 60 | 90 | 80 | 79 | 114 | 67 | 84 | 90 | 83.00 | 5.78 | |
| | compound | 57 | 5 | 5 | 5 | 10 | 130 | 75 | 85 | 46.50 | 16.84 | 0.0274 |
| seizure duration2 (SD2; sec) | control | 310 | 280 | 200 | 318 | 261 | 168 | 280 | 253 | 258.75 | 18.31 | |
| | compound | 180 | 5 | 5 | 5 | 10 | 130 | 275 | 235 | 105.63 | 40.33 | 0.0039 |
| afterdisch.dur.1 (ADD1; sec) | control | 71 | 90 | 80 | 93 | 114 | 67 | 84 | 89 | 86.00 | 5.15 | |
| | compound | 145 | 5 | 5 | 5 | 10 | 130 | 107 | 95 | 62.75 | 21.99 | n.s. |
| afterdisch.dur.2 (ADD2; sec) | control | 78 | 90 | 80 | 93 | 14 | 67 | 84 | 89 | 86.88 | 4.85 | |
| | compound | 145 | 5 | 5 | 5 | 10 | 130 | 107 | 95 | 62.75 | 21.99 | n.s. |
| BODY TEMP. | (° C.) | | | | | | | | | | | t-Test |
| control day | ante appl. | 38.5 | 38.4 | 38.2 | 38.6 | 39.0 | 38.5 | 38.2 | 38.2 | 38.45 | 0.10 | control |
| | 13' post appl. | 38.4 | 38.6 | 38.1 | 38.8 | 38.8 | 38.6 | 38.4 | 38.5 | 38.52 | 0.0 | n.s. |
| day of exper. | ante appl. | 38.4 | 38.7 | 38.7 | 38.9 | 39.1 | 38.4 | 38.6 | 38.9 | 38.71 | 0.09 | control |
| | 13' post appl. | 38.3 | 38.7 | 38.4 | 38.1 | 38.1 | 38.5 | 38.0 | 38.4 | 38.31 | 0.08 | 0.0236 |
| BEHAVIOR | (score) | | | | | | | | | | | |
| antaxia (1–6) | 13' | | | | | | | | | | | |
| abduct. hindlimb (1–3) | 13' | | | | | | | | | | | |
| red. righting (1–3) | 13' | | | | | | | | | | | |
| (flat body posture) (1–3) | 13' | | | | | | | | | | | |
| circling (1–3) | 13' | | | | | | | | | | | |
| Straub tail (1–3) | 13' | | | | | | | | | | | |
| pilorection (1–3) | 13' | | | | | | | | | | | |
| hypolocomotion (1–3) | 13' | | | | | | | | | | | |
| hyperlocomotion (1–3) | 13' | | | | | | | | | | | |

TABLE 7-continued

Anti-Seizure Activity And Adverse Effects of 2-propyl-4-hexynoic acid at 100 mg/kg

| animal | | 784 | 785 | 787 | 788 | 789 | 791 | 792 | 793 | X | S.E.M. | stat. sign. |
|---|---|---|---|---|---|---|---|---|---|---|---|---|
| muscle relaxation (1–3) | 13' | | | | | | | | | | | |
| rotarod-test day of exper. | 13' | + | + | + | + | + | + | + | + | 0% | | |

TABLE 8

Anti-Seizure Activity And Adverse Effects of 2-propyl-4-hexynoic acid at 200 mg/kg

| animal | | 784 | 785 | 787 | 788 | 789 | 791 | 792 | 793 | X | S.E.M. | stat. sign. |
|---|---|---|---|---|---|---|---|---|---|---|---|---|
| KINDLING | | | | | | | | | | | | Wilcoxon |
| afterdisch.thresh. | control | 42 | 20 | 30 | 15 | 30 | 200 | 90 | 36 | 57.88 | 21.87 | |
| (ADT; μA) | compound | 110 | 160 | 160 | 200 | 110 | 330 | 160 | 200 | 178.75 | 24.74 | 0.0039 |
| seizure severity | control | 5 | 5 | 5 | 5 | 4 | 3 | 5 | 5 | 4.63 | 0.26 | |
| (SS; score) | compound | 1 | 1 | 5 | 1 | 1 | 1 | 3 | 1 | 1.75 | 0.53 | 0.0078 |
| seizure duration1 | control | 50 | 65 | 87 | 82 | 47 | 10 | 62 | 90 | 61.63 | 9.34 | |
| (SD1; sec) | compound | 10 | 4 | 78 | 5 | 8 | 8 | 25 | 16 | 19.25 | 8.73 | 0.0039 |
| seizure duration2 | control | 298 | 240 | 224 | 210 | 120 | 10 | 290 | 191 | 197.88 | 33.41 | |
| (SD2; sec) | compound | 10 | 4 | 215 | 5 | 8 | | 25 | 16 | 36.38 | 25.63 | 0.0039 |
| afterdisch.dur.1 | control | 107 | 77 | 107 | 82 | 47 | 10 | 99 | 89 | 77.25 | 11.83 | |
| (ADD1;sec) | compound | 10 | 4 | 112 | 5 | 8 | | 25 | 16 | 23.50 | 12.87 | 0.0117 |
| afterdisch.dur.2 | control | 194 | 77 | 107 | 82 | 47 | 10 | 99 | 89 | 88.13 | 18.73 | |
| (ADD2; sec) | compound | 10 | 4 | 112 | 5 | 8 | 8 | 25 | 16 | 23.50 | 12.87 | 0.0117 |
| BODY TEMP. | (° C.) | | | | | | | | | | | t-Test |
| control day | ante appl. | 38.4 | 38.6 | 38.9 | 39.1 | 38.7 | 39.3 | 38.9 | 38.8 | 38.84 | 0.10 | control |
| | 13' post appl. | 38.8 | 38.7 | 38.3 | 38.2 | 37.9 | 38.5 | 38.1 | 38.4 | 38.36 | 0.11 | 0.0266 |
| day of exper. | ante appl. | 38.7 | 38.7 | 38.4 | 38.5 | 38.4 | 39.1 | 38.2 | 39.4 | 38.68 | 0.14 | control |
| | 13' post appl. | 37.4 | 38.5 | 38.0 | 38.0 | 37.4 | 38.4 | 38.0 | 37.8 | 37.94 | 0.14 | 0.0050 |
| BEHAVIOR | (score) | | | | | | | | | | | |
| antaxia (1–6) | 13' | 2 | 1 | 1 | 3 | 2 | 2 | | 1 | 1.50 | 0.33 | 0.0078 |
| abduct. hindlimb (1–3) | 13' | | | | | | | | | | | |
| red. righting (1–3) | 13' | 2 | 1 | | 1 | | 1 | | 1 | 0.75 | 0.25 | 0.0313 |
| (flat body posture) (1–3) | 13' | | | | | | | | | | | |
| circling (1–3) | 13' | | | | | | | | | | | |
| Straub tail (1–3) | 13' | | | | | | | | | | | |
| pilorection (1–3) | 13' | | | | | | | | | | | |
| hypolocomotion (1–3) | 13' | 2 | 2 | 1 | 2 | 1 | 1 | | 2 | 138 | 0.26 | 0.0078 |
| hypolocomotion (1–3) | 13' | | | | | | | | | | | |
| muscle relaxation (1–3) | 13' | 2 | 2 | 1 | 1 | 2 | 1 | | 2 | 1.38 | 0.26 | 0.0078 |
| rotarod-test day of exper. | 13' | + | + | + | + | + | + | + | + | 0% | | |

As shown in Table 9, plasma drug levels after administration of the same dose of valproic acid and 2-propyl-4-hexynoic acid were comparable. In addition, the drug solubility test shows that the concentrations for valproic acid and 2-propyl-4-hexynoic acid are 20 mg/ml and 18.5 mg/ml respectively. Therefore, there was no marked difference in the drug concentration between the two compounds in solution, suggesting that the differences in drug potency between the two compounds were not due to differences in solubililty.

TABLE 9

Plasma Drug Levels (in ug/ml)

| | Valproic Acid | 2-n-Propyl-4-Hexynoic Acid |
|---|---|---|
| 784 | 173.37 | 154.89 |
| 785 | 205.44 | 220.70 |
| 787 | 174.06 | 180.10 |
| 788 | 157.83 | 170.68 |
| 789 | 190.82 | 225.95 |

TABLE 9-continued

| | Plasma Drug Levels (in ug/ml) | |
|---|---|---|
| | Valproic Acid | 2-n-Propyl-4-Hexynoic Acid |
| 791 | 197.82 | 209.31 |
| 792 | 189.87 | 201.34 |
| 793 | 168.89 | 218.87 |
| Average | 182.26 | 198.37 |

What is claimed is:

1. A method of treating and/or preventing migraine in a mammal, comprising administering to said mammal a therapeutically effective amount of 2-n-propyl-4-hexynoic acid or a pharmaceutically compatible salt thereof, wherein the form of the 2-n-propyl-4-hexynoic acid is chosen from the racemate, a single enantiomer, or a non-racemic mixture of enantiomers.

2. The method of claim 1, wherein the compound is (R)-2-propyl-4-hexynoic acid.

3. The method of claim 1, wherein the compound is (S)-2-propyl-4-hexynoic acid.

4. The method of claim 1, wherein the compound is a pharmaceutically compatible salt of 2-propyl-4-hexynoic acid.

5. The method of claim 2, wherein the compound is a pharmaceutically compatible salt of (R)-2-propyl-4-hexynoic acid.

6. The method of claim 3, wherein the compound is a pharmaceutically compatible salt of (S)-2-propyl-4-hexynoic acid.

7. The method according to claim 1, wherein the 2-n-propyl-4-hexynoic acid is administered by at least one method selected from the groups consisting of parentally, orally, intravenously, intramuscularly, subcutaneously and rectally.

8. The method according to claim 1, wherein the 2-n-propyl-4-hexynoic acid is used to prevent migraine.

9. The method according to claim 1, wherein the 2-n-propyl-4-hexynoic acid is administered at a dose of approximately 1 to 60 mg/kg/day.

10. The method according to claim 9, wherein the dose is at about 10–20 mg/kg/day.

* * * * *